United States Patent
Klokkers et al.

(10) Patent No.: US 6,395,297 B1
(45) Date of Patent: *May 28, 2002

(54) TRANSDERMAL PREPARATION CONTACTING A LORATIDINE METABOLITE WITH ANTIHISTAMINIC ACTIVITY

(75) Inventors: Karin Klokkers; Wilfried Fischer, both of Lenggries; Daniel Bracher, München, all of (DE)

(73) Assignee: Hexal AG, Holzkirchen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/572,771

(22) Filed: May 17, 2000

Related U.S. Application Data

(63) Continuation of application No. 08/849,206, filed as application No. PCT/EP95/04761 on Dec. 1, 1995, now Pat. No. 6,165,498.

(30) Foreign Application Priority Data

Dec. 1, 1994 (DE) .......................................... 44 42 999

(51) Int. Cl.[7] ................................................. A61K 9/70
(52) U.S. Cl. ....................................... 424/448; 424/449
(58) Field of Search .................................. 424/448, 449

(56) References Cited

U.S. PATENT DOCUMENTS

| 4,910,205 A | | 3/1990 | Kogan et al. |
| 5,364,628 A | | 11/1994 | Kissel et al. |
| 5,656,286 A | | 8/1997 | Miranda et al. |
| 6,165,498 A | * | 12/2000 | Klokkers et al. |

FOREIGN PATENT DOCUMENTS

| GB | 2 098 865 2 | 4/1982 |

OTHER PUBLICATIONS

Zhong and Blume. *Pharmazie*, vol. 49, pp. 736–739, 1994.
Quercia and Broisman. *Hospital Formulary*, vol. 28, No. 2, pp. 137–153, 1993.

* cited by examiner

*Primary Examiner*—Raj Bawa
(74) *Attorney, Agent, or Firm*—Brooks & Kushman P.C.

(57) ABSTRACT

A transdermal patch contains an active loratidine metabolite contained with polyacrylate polymer matrix. The transdermal patch provides pharmaceutically useful transdermal flux rates over time.

10 Claims, No Drawings

TRANSDERMAL PREPARATION CONTACTING A LORATIDINE METABOLITE WITH ANTIHISTAMINIC ACTIVITY

This application is a continuation of U.S. application Ser. No. 08/849,206, field Mar. 23, 1998 now U.S. Pat. No. 6,165,498, a 371 of PCT/EP95/04761 field Dec. 4, 1995 which claims priority to DE 44 42 999. 1.

BACKGROUND OF THE INVENTION

1. Field of the Invention

The invention relates to a pharmaceutical composition for systemic transdermal administration comprising an active loratidine metabolite as active ingredient.

2. Description of the Related Art

Loratidine (ethyl-[4-(8-chloro-6,11-dihydro-5H-benzo[5,6]cyclohepta[1,2-b]pyridin-11-ylidene)-1-piperidinecarboxylate]) is an antihistamine that is available commercially as syrup or in the form of tablets. The active ingredient is metabolised in the body.

There is now a need to improve the antihistaminic effect and to provide a systemic form of administration. In tests carried out for that purpose, it has, surprisingly, been established that an active loratidine metabolite has sufficient stability to be provided as active ingredient in a pharmaceutical composition for systemic transdermal administration.

DETAILED DESCRIPTION OF THE INVENTION

The problem underlying the invention is solved by a pharmaceutical composition for systemic transdermal administration that comprises an active loratidine metabolite as active ingredient. The antihistaminic effect of the active loratidine metabolite can be exploited for that pharmaceutical composition.

A loratidine metabolite can be obtained from Irotec Laboratories (County Cork, Ireland) and has the following formula:

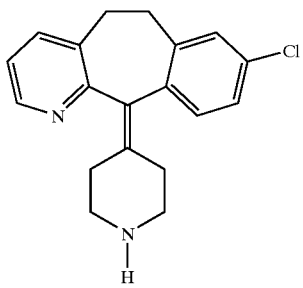

According to the invention, the pharmaceutical composition can be provided in the form of a customary liquid or solid form of systemic transdermal administration. For the relevant prior art, see, for example, DE-A-3 212 053, GB-A-2 098 865, Remington's Pharmaceutical Sciences, 16th edition, Mack-Verlag, and Sucker, Fuchs & Spieser, Pharmazeutische Technologie, 1st edition, Springer-Verlag.

The pharmaceutical composition according to the invention is customarily in the form of a viscous liquid, an ointment, a composition having a reservoir or a composition having a matrix. For example, the active loratidine metabolite may be present in a reservoir or matrix which are provided in the form of a gel or a polymer, for example in the form of a polymer according to EP-A-0 155 229.

According to a special embodiment, the pharmaceutical composition according to the invention may have a transdermal patch structure.

According to the invention, the patch structure can be provided by an acrylate-based matrix formed in customary manner on a carrier layer that is impermeable to water, it being possible to provide additionally a removable cover layer that protects the matrix.

According to the invention, the material of the matrix may be a non-swellable acrylate polymer, for example Durotack 280-2416 (Delft National Chemie, Zotphen, Netherlands).

The invention is explained hereinafter in greater detail by way of example.

In vitro test

A diffusion test is carried out in vitro according to Franz in J. Invest. Dermatol., 64 (1975) 194–195 and GB-A-2 098 865. For the test, the active loratidine metabolite is applied to one side of an isolated intact segment of mouse skin having a surface area of 2.5 cm$^2$. The other side of the skin segment is placed in contact with a 0.9% sodium chloride solution additionally containing 0.05% sodium azide. The amount of active ingredient that passes into the salt solution is monitored in customary manner by HPLC (HP Liquid Chromatography). Details are given below.

| Active loratidine metabolite | | 16.6 mg/ml |
|---|---|---|
| propylene glycol: water (1:1) | | 5.0 ml |

| Penetration rates per 2.5 cm$^2$ | time [h] | amount [μg/cm$^2$] | flow rate [μg/cm$^2$/24 h] |
|---|---|---|---|
| | 3 | 9.0 | 72 |
| | 6 | 85.1 | 341 |
| | 9 | 175.2 | 467 |
| | 14 | 333.6 | 572 |
| | 19 | 508.3 | 642 |
| | 24 | 578.8 | 579 |
| | 32 | 884.2 | 663 |

EXAMPLE 1

There is provided a transdermal therapeutic system of the reservoir type. For that purpose, a cover foil of 15 μm thick polyester material is used which may be provided with a skin-coloured coating or may be transparent. The cover foil is heat-moulded onto a laminate that consists of a microporous membrane, a self-adhesive contact adhesive from the group of acrylates, silicones and polyisobutylene with a tackifying resin, and a protective foil. The microporous membrane may be of the MSX 115 4P type may contain 28% EVA (ethylene vinyl acetate). The protective foil may be a polyester material, siliconised on one side, of 100 μm layer thickness. A cavity is left between the cover foil and the microporous membrane, which is filled with a saturated solution of the loratidine metabolite in a propylene gycol/water mixture (1:1).

EXAMPLE 2

| Loratidine metabolite | 20 g |
|---|---|
| Duro-Tak 1753 | 98.0 g |

The above-mentioned starting materials are mixed to form a clear solution. The solution is applied to a siliconised foil or paper to produce a content per surface area of 100 g/m². A transparent polypropylene or polyester foil is laminated onto the dried matrix. The finished patches are punched out of the laminate in sizes of from 10 cm² (corresponding to 2 mg of active ingredient) to 40 cm² (corresponding to 8 mg of active ingredient).

What is claimed is:

1. A transdermal patch suitable for transdermal administration of an active loratidine metabolite, said transdermal patch comprising said active loratidine metabolite contained in a polymer matrix, the polymers of said polymer matrix consisting essentially of acrylate polymers.

2. The transdermal patch of claim 1, wherein said acrylate polymer is a non-swellable acrylate polymer.

3. The transdermal patch of claim 1, wherein said active loratidine metabolite has the structure

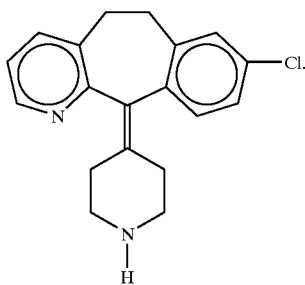

4. The transdermal patch of claim 1, further comprising a water impermeable cover layer on a surface of said transdermal patch most remote from the surface of said transdermal patch to be applied to the skin; and a microporous membrane on the surface of the transdermal to be applied to the skin, said microporous membrane having attached thereto an exterior contact adhesive.

5. The transdermal patch of claim 4 wherein said microporous membrane is an ethylene-vinyl acetate copolymer-containing membrane.

6. A process of administering an active loratidine metabolite to a patient in need thereof, said process comprising applying to the skin of said patient the transdermal patch of claim 1.

7. A process of administering an active loratidine metabolite to a patient in need thereof, said process comprising applying to the skin of said patient the transdermal patch of claim 2.

8. A process of administering an active loratidine metabolite to a patient in need thereof, said process comprising applying to the skin of said patient the transdermal patch of claim 3.

9. A process of administering an active loratidine metabolite to a patient in need thereof, said process comprising applying to the skin of said patient the transdermal patch of claim 4.

10. A process of administering an active loratidine metabolite to a patient in need thereof, said process comprising applying to the skin of said patient the transdermal patch of claim 5.

* * * * *